United States Patent [19]

Carignan

[11] Patent Number: 4,787,907
[45] Date of Patent: Nov. 29, 1988

[54] MORSE TAPER
[75] Inventor: Roger G. Carignan, Camarillo, Calif.
[73] Assignee: Techmedica, Inc., Camarillo, Calif.
[21] Appl. No.: 10,473
[22] Filed: Feb. 3, 1987
[51] Int. Cl.[4] ............................................. A61F 2/30
[52] U.S. Cl. ...................................................... 623/18
[58] Field of Search ................. 403/16, 354, 361, 334, 403/356; 128/92 YZ; 623/22, 23, 16-21

[56] References Cited

U.S. PATENT DOCUMENTS

| | | | |
|---|---|---|---|
| 3,818,513 | 6/1974 | Pillet | 623/18 |
| 3,979,779 | 9/1976 | Zeibig | 623/18 |
| 3,990,116 | 11/1976 | Fixel | 623/18 |
| 4,016,874 | 4/1977 | Maffei | 128/92 YZ |
| 4,158,895 | 6/1979 | Resuich | 623/16 |
| 4,467,794 | 8/1984 | Maffei | 128/92 YZ |
| 4,629,463 | 12/1986 | Grundei | 128/92 YZ |
| 4,677,972 | 7/1987 | Tornier | 623/22 |

FOREIGN PATENT DOCUMENTS

| | | | |
|---|---|---|---|
| 0121491 | 10/1984 | European Pat. Off. | 623/22 |
| 200672 | 11/1986 | European Pat. Off. | 623/23 |

OTHER PUBLICATIONS

"Machinist's Handbook", 20th Edition, p. 1730, 1980.

Primary Examiner—Richard J. Apley
Assistant Examiner—James Prizant
Attorney, Agent, or Firm—Cislo & Thomas

[57] ABSTRACT

An improved Morse taper consisting essentially of a male taper and a mating female taper, one of the tapers having a key recess at the periphery of a mating face such that a key can be inserted and rotated to force the segments longitudinally apart from its assembled embodiment such tapers are particularly useful in skeletal structures. A distraction key with a cam designed to fit in and rotate in the key recess is also described.

4 Claims, 2 Drawing Sheets

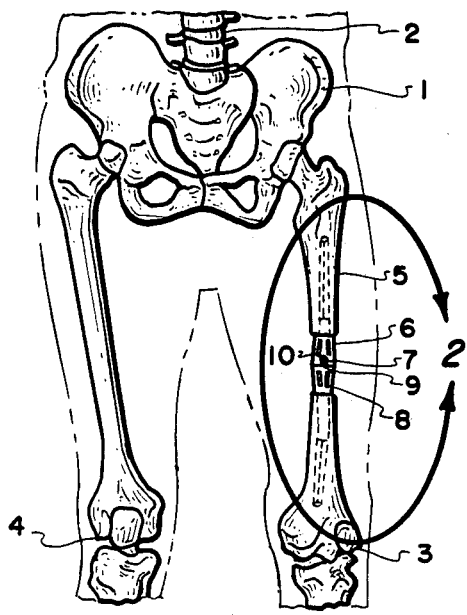
Fig. 1
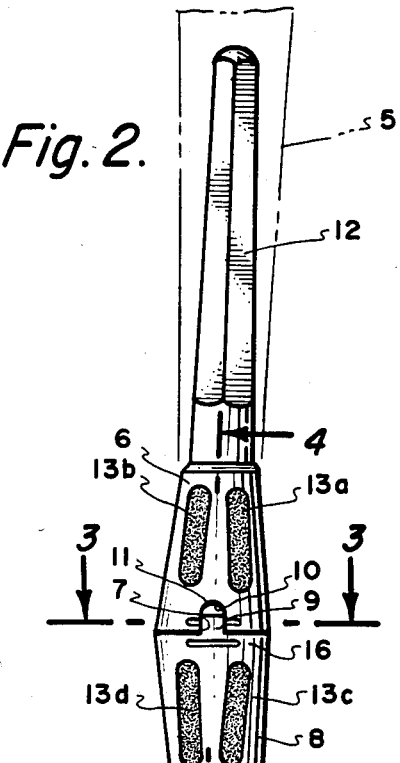
Fig. 2
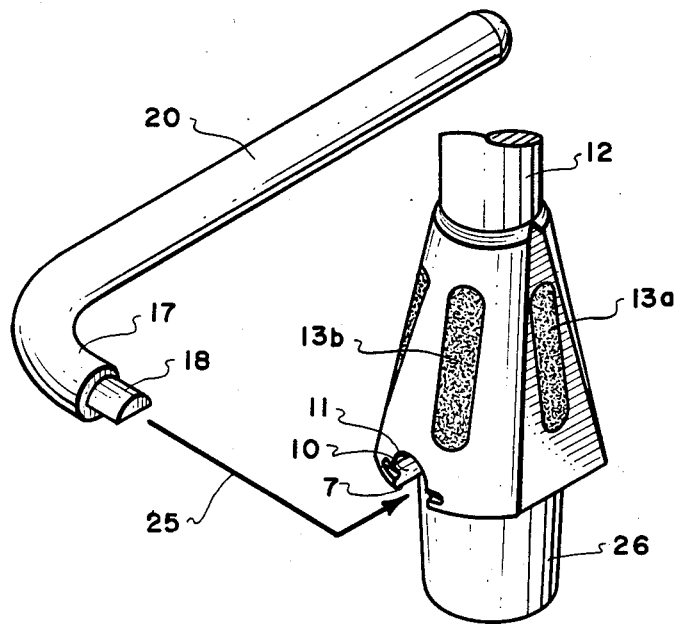
Fig. 6
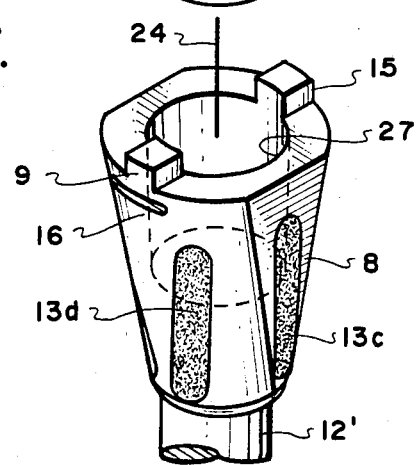
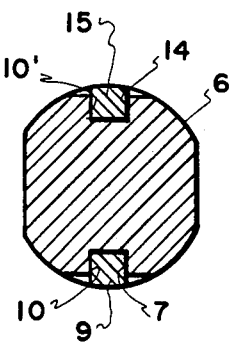
Fig. 3

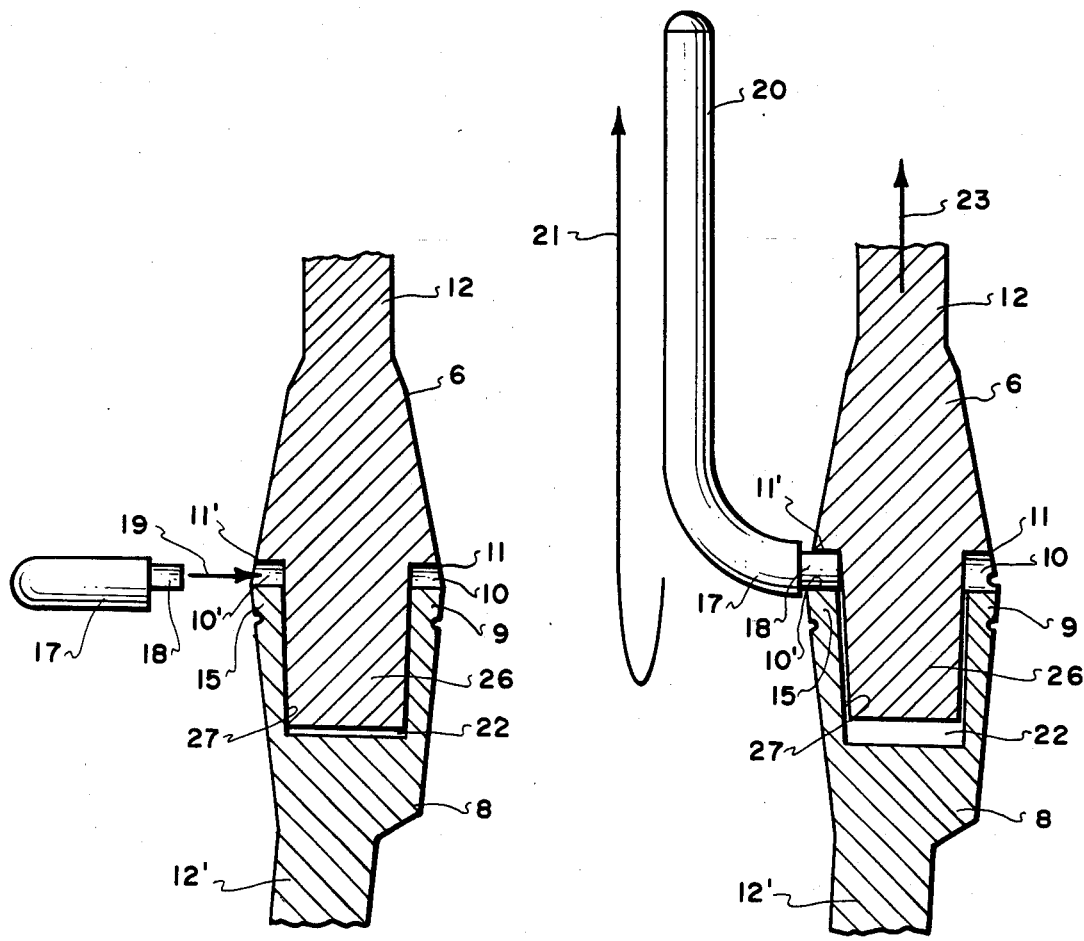

MORSE TAPER

RELATED APPLICATION

Co-pending application Ser. No. 804,927, (now U.S. pat. 4,636,219) filed Dec. 5, 1985 and entitled Bone Prosthesis Device and this application have a common assignee and Roger Carignan, the sole inventor of this application, is a co-inventor in the earlier filed application.

BACKGROUND OF THE INVENTION

This invention relates to Morse tapers, used in prosthetic devices for replacement, reconstruction and attachment in the skeletal system of humans and animals. More particularly, it relates to improved orthopedic tapers, especially tapers that may be used in the arms or legs of humans. These devices are employed as a replacement for a joint, such as a hip or shoulder, or they may replace a segment of bone.

The invention is particularly concerned with a structure that is known as a Morse taper. This structure consists essentially of two segments; one segment has a male taper and the other segment has a mating female taper. When the two segments are assembled, they form an extremely close fit, and this creates a problem, if for any reason, the physician wishes to separate them again. For example, if one of them is not properly aligned with the other one, it will be necessary to separate them to realign the two components. In the Morse tapers of the prior art, this has been very difficult to do without significantly damaging at least one of the segments of the taper.

OBJECTS OF THE INVENTION

It is an object of this invention to modify the Morse taper in such a way that the components can be separated with ease.

It is a further object of this invention to provide a key recess at the mating faces of the taper segments so that a key can be inserted and rotated to exert disassociation forces to separate the two components.

It is a further object of this invention to provide a Morse taper system employing a cooperative notch so that a key with a cam on one end can be inserted in the notch for rotation and separation of the Morse components making up the system by reason of the application of longitudinally orientated disassociation forces.

BRIEF DESCRIPTION OF THE INVENTION

The invention is concerned with an improved Morse taper consisting essentially of a male taper segment and a mating female taper segment wherein a notch or key recess is provided on the periphery of and at the mating face of at least one segment such that a key can be inserted and rotated to cause the two segments to separate. Such tapers are especially useful in skeletal replacement structures. In a preferred embodiment the Morse segment without the notch has an interfitting lug that is substantially the width of the notch but not as long. The key recess, in this case, is the space between the top of the lug and the top of the notch. The invention is further concerned with the design of a key which has an appropriate cam at one end.

BRIEF DESCRIPTION OF THE DRAWINGS

FIG. 1 is a perspective view of part of a human skeleton showing the bone structure from the lower vertebrae through the knee joints with an orthopedic taper device in the left femur.

FIG. 2 is an enlarged elevational view of the bone structure and taper circumscribed by line 2 in FIG. 1.

FIG. 3 is a cross-sectional view along line 3—3 in FIG. 2.

FIG. 4 is a cross-sectional view along line 4—4 in FIG. 2.

FIG. 5 is a cross-sectional view as in FIG. 4 but showing the distraction key inserted and rotated 90°.

FIG. 6 is an exploded view showing the relationship of the distraction key and a recess in the upper segment of the orthopedic taper.

DESCRIPTION OF THE INVENTION

Referring to the drawings in which like numerals designate like elements throughout, FIG. 1 portrays the lower skeletal structure 1 of a human from the lower vertebrae 2 through the left and right knee joints 3 and 4, respectively. Within the area encompassed by a circular line 2 is a portion of the left femur 5 including a taper of the present invention consisting of taper segment 6 in which there is notch 7 and taper segment 8 which has lug 9. As assembled, the notch and lug are substantially of equal width but of different lengths resulting in key recess 10.

Referring to FIG. 2 which discloses an enlarged elevational view of a portion of the left femur 5 an a preferred embodiment of the present invention, the relationship of taper segment 6, taper segment 8, notch 7 and lug 9 are set forth with greater clarity, and key recess 10 as well as its curved upper surface 11 are apparent. In this instance, the taper segments 6 and 8 have extensions 12 and 12' which form tight fits in the medullary canal of the upper and lower portions of femur 5. Also shown are titanium alloy mesh sections 13a, 13b, 13c and 13d which help to secure the Morse taper device by allowing tissue and/or bone to expand and grow into the mesh sections. Such mesh sections are described in more detail in co-pending application Ser. No. 804,927, filed Dec. 5, 1985, of which I am a co-inventor.

FIG. 3 illustrates another variation of the present invention. It shows in cross-section the taper segment 6, notch 7 and lug 9. In addition, it shows a second notch 14 and a second lug 15. This variation provides two key recess 10 and 10', approximately 180° from each other on the circumference of the taper. Segments 6 and 8 can be separated more easily by putting a distraction key into recesses 10 and 10', either simultaneously or seriatim. When two keys are used, the pressure on the upper segment 6 to separate it from the lower segment 8 is in better balance and causes the segments to separate with minimum strain. This allows disassociation without damaging the device or exerting strain on the interface between the stem of the device and the bone into which it fits. The modification using lug 9, and preferably with lug 15, facilitates the alignment of the two segments and eliminates any tendency that one segment might rotate out of alignment with the second segment.

In another modification of the invention, taper segment 8 may be formed without any lugs. In this situation, adjustment has to be made in the size of notch 7 or the insertion cam on the distraction key (described below) so that a snug fit is formed between the cam, the upper surface of notch 7 and face 16 of taper segment 8.

FIG. 4 is a cross-sectional view along line 4—4 in FIG. 2 showing in more detail the assembled relationship of taper segment 6 and taper segment 8 as well as recesses 10 and 10'. In addition, FIG. 4 shows a portion of distraction key 17 and cam 18 on one end of the key. Arrow 19 shows the direction in which cam 18 will be inserted into recess 10'. Cam 18 is designed to fit snugly into key recess 10 or 10'; accordingly, recess 10 and 10' have curved upper surfaces 11 and 11' so that the key will push against both segments 6 and 8 when it is rotated.

FIG. 5 shows the same cross-sectional view as FIG. 4 except that distraction key 17 has been inserted into key recess 10' and rotated 90°, illustrated at arrow 21. In this view, handle 20 of distraction key 17 is illustrated, and in addition the separation between taper segment 6 and taper segment 8 caused by the rotation of the handle is visible at space 22. Taper segment 6 has been moved upward as illustrated at arrow 23.

FIG. 6 is an exploded view showing segments 6 and 8 in position to be assembled as indicated by arrow 24 and the relationship of distraction key 17, cam 18 and recess 10 in taper segment 6 as indicated by arrow 24. There is an extension 26 on the base of taper segment 6 and an opening in taper segment 8. When taper segments 6 and 8 are assembled, extension 26 fits snugly into opening 27.

While the invention has been described with relation to a prosthetic device for a human femur, it will be recognized that the present invention may be used for other areas where Morse tapers are found as well as for prosthetic devices elsewhere throughout the human body or in the body of an animal. For example, it can be used wherein one segment simulates the end of the bone structure. In the event, a segment is to replace a hip joint, it will not have extension 11 but will be fashioned so that end fits into the hip socket as a natural bone would.

Since orthopedic devices for replacement, reconstruction and attachment in skeleton systems have been in use for an extended number of years, the method of making them and the materials that may be used are well-known to those skilled in the art. The method for making the distraction key and cam also will be obvious to any machinist of ordinary skill; the materials will preferably be those ordinary used in surgical tools; for example, titanium or cobat-chrome alloys.

While the invention has been described as having the notch or key recess entirely in one segment, it is possible, in those variations without interfitting lugs, to have the notch partially in both faces. In such an event, care must be taken to assemble the segments so that the partial notches in each are properly aligned.

Various modifications and changes will be obvious to those of ordinary skill in the art, and all such changes and variations not deviating from the spirit and essence of the invention are intended to be covered by the appended claims.

I claim:

1. An improved orthopedic taper joint for holding two bones together comprising two segments, one segment having a cylindrical male taper narrower at its connecting end and the other segment having a mating female taper wider at its connecting end, each segment having a face around the taper such that said faces are opposing when said segments are assembled, wherein a recess is located on the periphery of one of said faces such that a rotatable key can be inserted and rotated to force said segments longitudinally apart to disconnect the two bones held together, and wherein an interfitting lug is positioned on the face opposite the face defining said recess, said lug being substantially the width of said recess, but shorter than the depth of said recess, causing the formation of a slot between the end of the lug and the bottom of said recess when assembled, and wherein said rotatable key has a cam mounted on one end of a handle, wherein said cam is sized to fit within said slot and is rotatable therein, and wherein said segments have retaining wire mesh sections along the sides of said segments to allow tissue and bone to grow into said wire mesh sections and securely affix said structure to the bones to be joined.

2. An improved orthopedic taper structure as claimed in claim 1, wherein said segments have extending ends having flattened sides which are received and held with the ends of the bones to be joined by the taper structure.

3. An improved orthopedic taper structure as claimed in claim 2, wherein said segments have exposed slots on the exterior sides of said segments.

4. A bone joint comprising the combination: a first segment having an extending portion to be received within a bone cavity and terminating in an enlarged head portion having an inner set depending taper narrowest at its terminus; and a second segment having an extending portion to be received within a bone cavity and having an opposed enlarged head portion having a recess adapted to receive said inner set depending taper in mating engagement, one of said enlarged head portions having a slot for receiving a tool such that upon rotation of said tool longitudinal forces are imparted to each of said first and second segments to separate the same.

* * * * *